US008197474B2

(12) United States Patent
Scarborough et al.

(10) Patent No.: US 8,197,474 B2
(45) Date of Patent: Jun. 12, 2012

(54) VOLUME MAINTAINING OSTEOINDUCTIVE/OSTEOCONDUCTIVE COMPOSITIONS

(75) Inventors: Nelson L. Scarborough, Andover, MA (US); Sergio J. Gadeleta, Doylestown, PA (US); David R. Kaes, Toms River, NJ (US); Albert Manrique, Aberdeen, NJ (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 13/185,553

(22) Filed: Jul. 19, 2011

(65) Prior Publication Data

US 2011/0274668 A1 Nov. 10, 2011

Related U.S. Application Data

(63) Continuation of application No. 12/548,029, filed on Aug. 26, 2009, now Pat. No. 8,002,813, which is a continuation of application No. 11/284,539, filed on Nov. 22, 2005, now abandoned, which is a continuation of application No. 10/413,324, filed on Apr. 14, 2003, now abandoned, which is a continuation of application No. PCT/US00/28462, filed on Oct. 13, 2000.

(60) Provisional application No. 60/159,774, filed on Oct. 15, 1999.

(51) Int. Cl.
*A61F 2/28* (2006.01)

(52) U.S. Cl. ......... 606/33; 424/93.7; 424/422; 435/325; 606/909

(58) Field of Classification Search .................. None
See application file for complete search history.

(56) References Cited

U.S. PATENT DOCUMENTS

| | | | |
|---|---|---|---|
| 159,334 A | 2/1875 | Kumpf | |
| 781,882 A | 2/1905 | Hunter | |
| 2,516,438 A | 7/1950 | Wheeler | |
| 2,968,593 A | 1/1961 | Rapkin | |
| 3,458,397 A | 7/1969 | Myers et al. | |
| 3,609,867 A | 10/1971 | Hodosh | |
| 3,739,773 A | 6/1973 | Schmitt et al. | |
| 3,790,507 A | 2/1974 | Hodosh | |
| 3,829,904 A | 8/1974 | Ling et al. | |
| 3,891,997 A | 7/1975 | Herbert | |
| 3,922,726 A | 12/1975 | Trentani et al. | |
| 3,947,287 A | 3/1976 | Belde et al. | |
| 4,059,684 A | 11/1977 | Gross et al. | |
| 4,123,806 A | 11/1978 | Amstutz et al. | |
| 4,134,792 A | 1/1979 | Boguslaski et al. | |
| 4,172,128 A | 10/1979 | Thiele et al. | |
| 4,191,747 A | 3/1980 | Scheicher | |
| 4,209,434 A | 6/1980 | Wilson et al. | |
| 4,224,698 A | 9/1980 | Hopson | |
| 4,291,013 A | 9/1981 | Wahlig et al. | |
| 4,294,753 A | 10/1981 | Urist | |
| 4,355,331 A | 10/1982 | Georges et al. | |
| 4,363,319 A | 12/1982 | Altshuler | |
| 4,394,370 A | 7/1983 | Jefferies | |
| 4,430,760 A | 2/1984 | Smestad | |
| 4,440,370 A | 4/1984 | Rood | |
| 4,440,750 A | 4/1984 | Glowacki et al. | |
| 4,450,592 A | 5/1984 | Niederer et al. | |
| 4,458,733 A | 7/1984 | Lyons | |
| 4,472,840 A | 9/1984 | Jefferies | |
| 4,485,097 A | 11/1984 | Bell | |
| 4,512,038 A | 4/1985 | Alexander et al. | |
| 4,516,276 A | 5/1985 | Mittelmeier et al. | |
| 4,563,350 A | 1/1986 | Nathan et al. | |
| 4,563,489 A | 1/1986 | Urist | |
| 4,581,030 A | 4/1986 | Bruns et al. | |
| 4,595,713 A | 6/1986 | St. John | |
| 4,620,327 A | 11/1986 | Caplan et al. | |
| 4,623,553 A | 11/1986 | Ries et al. | |
| 4,627,853 A | 12/1986 | Campbell et al. | |
| 4,636,526 A | 1/1987 | Dorman et al. | |
| 4,637,931 A | 1/1987 | Schmitz | |
| 4,678,470 A | 7/1987 | Nashef et al. | |
| 4,698,375 A | 10/1987 | Dorman et al. | |
| 4,709,703 A | 12/1987 | Lazarow et al. | |
| 4,743,259 A | 5/1988 | Bolander et al. | |
| 4,795,463 A | 1/1989 | Gerow | |
| 4,795,467 A | 1/1989 | Piez et al. | |
| 4,824,939 A | 4/1989 | Simpson | |
| 4,842,604 A | 6/1989 | Dorman et al. | |
| 4,857,269 A | 8/1989 | Wang et al. | |
| 4,863,472 A | 9/1989 | Tormala et al. | |
| 4,888,366 A | 12/1989 | Chu et al. | |
| 4,902,296 A | 2/1990 | Bolander et al. | |
| 4,919,939 A | 4/1990 | Baker | |
| 4,932,973 A | 6/1990 | Gendler | |

(Continued)

FOREIGN PATENT DOCUMENTS

DE 179 833 2/1905

(Continued)

OTHER PUBLICATIONS

Abel, E. "The vapor phase above the system sulfuric acid-water." J. Phys. Chem. 50(3), pp. 260-283 (1946).
Abjornson et al., "A Novel Approach to Bone Grafting Substitutes", Society for Biomaterials, p. 1372 (2000).
Block, Michael S., D.M.D. et al., "Bone Maintenance 5 to 10 years After Sinus Grafting", J. Oral Maxillofacial Surg., vol. 56, pp. 706-714, 1998.
Bobyn et al., "The Optimum Pore Size for the Fixation of Porous-Surfaced Metal Implants by Ingrowth of Bone", Clinical Orthopaedics and Related Research, 1980, pp. 263-270.
Bolander et al.,"The Use of Demineralized Bone Matrix ion te Repair of Segmental Defects", *The Journal of Bone and Joint Surgery*, vol. 68-A, No. 8, pp. 1264-1273.

(Continued)

*Primary Examiner* — Lora E Barnhart Driscoll

(57) ABSTRACT

An osteoinductive/osteoconductive composition prepared from a quantity, of demineralized fibrous bone elements possessing an average surface area to volume ratio of about 100:1 to about 20:1, a quantity of mostly shaped regular non-fibrous bone elements possessing an average surface area to volume ratio of about 10:1 or less and a sufficient quantity of biocompatible fluid carrier sufficient to provide the composition as a deformable mass is provided herein. Also provided is a method of using the composition to repair a bone defect site.

8 Claims, 5 Drawing Sheets

U.S. PATENT DOCUMENTS

| | | |
|---|---|---|
| 4,946,792 A | 8/1990 | O'Leary |
| 4,950,296 A | 8/1990 | McIntyre |
| 4,961,707 A | 10/1990 | Magnusson et al. |
| 4,975,526 A | 12/1990 | Kuberasampath et al. |
| 4,994,030 A | 2/1991 | Glowczewskie, Jr. et al. |
| 5,001,169 A | 3/1991 | Nathan et al. |
| 5,007,930 A | 4/1991 | Dorman et al. |
| 5,015,247 A | 5/1991 | Michelson |
| 5,032,445 A | 7/1991 | Scantlebury et al. |
| 5,053,049 A | 10/1991 | Campbell |
| 5,073,373 A | 12/1991 | O'Leary |
| 5,092,887 A | 3/1992 | Gendler |
| 5,108,399 A | 4/1992 | Eitenmuller et al. |
| 5,112,354 A | 5/1992 | Sires |
| 5,123,925 A | 6/1992 | Smestad et al. |
| 5,139,527 A | 8/1992 | Redl et al. |
| 5,162,114 A | 11/1992 | Kuberasampath et al. |
| 5,171,278 A | 12/1992 | Pisharodi |
| 5,171,574 A | 12/1992 | Kuberasampath et al. |
| 5,197,882 A | 3/1993 | Jernberg |
| 5,207,710 A | 5/1993 | Chu et al. |
| 5,236,456 A | 8/1993 | O'Leary et al. |
| 5,284,655 A | 2/1994 | Bogdansky et al. |
| 5,290,558 A | 3/1994 | O'Leary et al. |
| 5,298,254 A | 3/1994 | Prewett et al. |
| 5,306,304 A | 4/1994 | Gendler |
| 5,314,476 A | 5/1994 | Prewett et al. |
| 5,314,478 A | 5/1994 | Oka et al. |
| 5,329,846 A | 7/1994 | Bonutti |
| 5,336,507 A | 8/1994 | Sottosanti |
| 5,343,877 A | 9/1994 | Park |
| 5,366,507 A | 11/1994 | Sottosanti |
| 5,368,859 A | 11/1994 | Dunn et al. |
| 5,405,390 A | 4/1995 | O'Leary et al. |
| 5,405,402 A | 4/1995 | Dye et al. |
| 5,425,639 A | 6/1995 | Anders |
| 5,425,762 A | 6/1995 | Muller |
| 5,432,000 A | 7/1995 | Young et al. |
| 5,439,684 A | 8/1995 | Prewett et al. |
| 5,441,517 A | 8/1995 | Kensey et al. |
| 5,447,725 A | 9/1995 | Damani et al. |
| 5,449,375 A | 9/1995 | Vidal et al. |
| 5,455,041 A | 10/1995 | Genco et al. |
| 5,464,439 A | 11/1995 | Gendler |
| 5,476,880 A | 12/1995 | Cooke et al. |
| 5,480,436 A | 1/1996 | Bakker et al. |
| 5,484,601 A | 1/1996 | O'Leary et al. |
| 5,490,962 A | 2/1996 | Cima et al. |
| 5,496,375 A | 3/1996 | Sisk |
| 5,507,813 A | 4/1996 | Dowd et al. |
| 5,510,396 A | 4/1996 | Prewett et al. |
| 5,518,680 A | 5/1996 | Cima et al. |
| 5,531,791 A | 7/1996 | Wolfinbarger, Jr. |
| 5,545,222 A | 8/1996 | Bonutti |
| 5,556,430 A | 9/1996 | Gendler |
| 5,567,806 A | 10/1996 | Abdul-Malak et al. |
| 5,607,269 A | 3/1997 | Dowd et al. |
| 5,641,518 A | 6/1997 | Badylak et al. |
| 5,656,593 A | 8/1997 | Kuberasampath et al. |
| 5,662,710 A | 9/1997 | Bonutti |
| 5,676,146 A | 10/1997 | Scarborough |
| 5,683,459 A | 11/1997 | Brekke |
| 5,700,479 A | 12/1997 | Lundgren |
| 5,707,962 A | 1/1998 | Chen et al. |
| 5,723,117 A | 3/1998 | Nakai et al. |
| 5,727,945 A | 3/1998 | Dannenbaum |
| 5,782,919 A | 7/1998 | Zdeblick et al. |
| 5,807,437 A | 9/1998 | Sachs et al. |
| 5,846,484 A | 12/1998 | Scarborough et al. |
| 5,888,219 A | 3/1999 | Bonutti |
| 5,899,939 A | 5/1999 | Boyce et al. |
| 5,910,315 A | 6/1999 | Stevenson et al. |
| 5,922,753 A | 7/1999 | Petrie et al. |
| 6,030,635 A | 2/2000 | Gertzman et al. |
| 6,090,998 A | 7/2000 | Grooms et al. |
| 6,123,731 A | 9/2000 | Boyce et al. |
| 6,132,472 A | 10/2000 | Bonutti |
| 6,206,923 B1 | 3/2001 | Boyd et al. |
| 6,224,630 B1 | 5/2001 | Bao et al. |
| 6,294,187 B1 | 9/2001 | Boyce et al. |
| 6,311,690 B1 | 11/2001 | Jefferies |
| 6,326,018 B1 | 12/2001 | Gertzman et al. |
| 6,340,477 B1 | 1/2002 | Anderson |
| 6,361,565 B1 | 3/2002 | Bonutti |
| 6,375,663 B1 | 4/2002 | Ebner et al. |
| 6,432,436 B1 | 8/2002 | Gertzman et al. |
| 6,436,138 B1 | 8/2002 | Dowd et al. |
| 6,436,139 B1 | 8/2002 | Shapiro et al. |
| 6,437,018 B1 | 8/2002 | Gertzman et al. |
| 6,458,375 B1 | 10/2002 | Gertzman et al. |
| 6,599,515 B1 | 7/2003 | Delmotte |
| 6,599,520 B2 | 7/2003 | Scarborough et al. |
| 6,616,698 B2 | 9/2003 | Scarborough |
| 6,630,153 B2 | 10/2003 | Long et al. |
| 6,632,247 B2 | 10/2003 | Boyer, II et al. |
| 6,638,309 B2 | 10/2003 | Bonutti |
| 6,652,592 B1 | 11/2003 | Grooms et al. |
| 6,652,593 B2 | 11/2003 | Boyer, II et al. |
| 6,706,067 B2 | 3/2004 | Shimp et al. |
| RE38,522 E | 5/2004 | Gertzman et al. |
| 6,733,534 B2 | 5/2004 | Sherman |
| 6,736,853 B2 | 5/2004 | Bonutti |
| 6,776,938 B2 | 8/2004 | Bonutti |
| 6,808,585 B2 | 10/2004 | Boyce et al. |
| 6,843,807 B1 | 1/2005 | Boyce et al. |
| 6,855,169 B2 | 2/2005 | Boyer, II et al. |
| 6,863,694 B1 | 3/2005 | Boyce et al. |
| 6,911,212 B2 | 6/2005 | Gertzman et al. |
| 6,913,621 B2 | 7/2005 | Boyd et al. |
| 7,045,141 B2 | 5/2006 | Merboth et al. |
| 7,163,691 B2 | 1/2007 | Knack et al. |
| RE39,587 E | 4/2007 | Gertzman et al. |
| 7,311,713 B2 | 12/2007 | Johnson et al. |
| 7,323,193 B2 | 1/2008 | Morris et al. |
| 2001/0020186 A1 | 9/2001 | Boyce |
| 2002/0026244 A1 | 2/2002 | Trieu |
| 2002/0029084 A1 | 3/2002 | Paul |
| 2002/0035401 A1 | 3/2002 | Boyce et al. |
| 2002/0055143 A1 | 5/2002 | Bell et al. |
| 2002/0107570 A1 | 8/2002 | Sybert et al. |
| 2002/0120338 A1 | 8/2002 | Boyer, II et al. |
| 2002/0161449 A1 | 10/2002 | Muschler |
| 2003/0009235 A1 | 1/2003 | Manrique et al. |
| 2003/0036800 A1 | 2/2003 | Meredith |
| 2003/0045934 A1 | 3/2003 | Bonutti |
| 2003/0093154 A1 | 5/2003 | Estes et al. |
| 2004/0023387 A1 | 2/2004 | Morris et al. |
| 2004/0097612 A1 | 5/2004 | Rosenberg et al. |
| 2004/0220681 A1 | 11/2004 | Cole et al. |
| 2005/0065214 A1 | 3/2005 | Kronenthal |
| 2005/0170396 A1 | 8/2005 | Baker et al. |
| 2006/0002976 A1 | 1/2006 | Kronenthal |
| 2006/0013857 A1 | 1/2006 | Kronenthal |
| 2006/0030948 A1 | 2/2006 | Manrique et al. |
| 2006/0147545 A1 | 7/2006 | Scarborough et al. |
| 2006/0280801 A1 | 12/2006 | Kronenthal |

FOREIGN PATENT DOCUMENTS

| | | |
|---|---|---|
| DE | 44 34 459 | 4/1996 |
| DE | 29608321 | 8/1996 |
| EP | 0 082 621 | 6/1983 |
| EP | 0 243 151 | 10/1987 |
| EP | 0 267 015 | 5/1988 |
| EP | 0 321 442 A3 | 6/1989 |
| EP | 0 366 029 A3 | 5/1990 |
| EP | 0 406 856 | 1/1991 |
| EP | 0405429 | 1/1991 |
| EP | 0 411 925 | 2/1991 |
| EP | 0 413 492 | 2/1991 |
| EP | 0 419 275 | 3/1991 |
| EP | 0 483 944 | 5/1992 |
| EP | 0 495 284 | 7/1992 |
| EP | 0 520 237 | 12/1992 |
| EP | 0 555 807 | 8/1993 |
| EP | 0 567 391 | 10/1993 |
| EP | 0 693 523 | 1/1996 |
| EP | 1 142 581 A2 | 10/2001 |

| | | |
|---|---|---|
| FR | 2691901 | 12/1993 |
| GB | 2175807 | 10/1986 |
| JP | 9059/1986 | 3/1986 |
| JP | 2121652 | 5/1990 |
| JP | 3210270 A | 9/1991 |
| JP | 4097747 A | 2/1992 |
| JP | 9506281 | 6/1997 |
| RU | 0880425 | 11/1981 |
| WO | WO 86/07265 | 12/1986 |
| WO | WO 89/04646 | 6/1989 |
| WO | WO 89/11880 | 12/1989 |
| WO | WO94/21196 | 9/1994 |
| WO | WO 95/15776 | 6/1995 |
| WO | WO 96/39203 | 12/1996 |
| WO | WO 97/25941 | 7/1997 |
| WO | WO 98/00183 | 1/1998 |
| WO | WO98/17209 | 4/1998 |
| WO | WO 98/40113 | 9/1998 |
| WO | WO 99/39757 A1 | 8/1999 |
| WO | WO 00/34556 | 6/2000 |
| WO | WO 00/35510 | 6/2000 |
| WO | WO 00/50102 | 8/2000 |
| WO | WO 01/008584 | 8/2001 |
| WO | WO 02/02156 | 1/2002 |
| WO | WO 02/47587 A | 6/2002 |
| WO | WO 2004/108023 A | 12/2004 |
| WO | WO 2006/057011 A2 | 6/2006 |
| WO | WO 2006/076712 A2 | 7/2006 |

OTHER PUBLICATIONS

Bostrom et al., "Use of Bone Morphogeneic Protein-2 in the Rabbit Ulnar Nonunion Model", Clinical Orthopaedics and Related Research, No. 327, pp. 272-282 (1996).
Covey et al., "Clinical Induction of Bone Repair with Demineralized Bone Matrix or a Bone Morphogenetic Protein", Orthopaedic Review, Aug. 1989, vol. XVIII, No. 8, pp. 857-863.
Crowe et al., "Inhibition of Enzymatic Digestion of Amylose by Free Fatty Acids in Vitro Contributes to Resistant Starch Formation", J. Nutr. 130(8): 2006-2008, 2000.
Edwards et al., "Osteoinduction of Human Demineralized Bone: Characterization in a Rat Model", *Clinical Orthopaedics & Rel. Res.*357:219-228, Dec. 1998.
Gekko et al., "Mechanism of Protein Stabilization by Glycerol: Preferential Hydration in Glycerol-Water Mixtures", vol. 20, No. 16, pp. 4667-5676 (1981).
Gepstein et al., "Bridging Large Defects in Bone by Demineralized Bone Matrix in the Form of a Powder", *The Journal of Bone and Joint Surgery*, vol. 69-A, No. 7, pp. 984-991, 1987.
Gher, Marlin E., et al., "Bone Grafting and Guided Bone Regeneration for Immediate Dental Implants in Humans", J. Periodontology, 1994, 65:881-891.
Glowacki et al., "Application of Biological Principle of Induced Osteogenesis for Craniofacial Defects", The Lancet, 1981, vol. 1, No. 8227, pp. 959-962.
Glowacki et al., "Demineralized Bone Implants", *Symposium on Horizons in Plastic Surgery*, vol. 12, No. 2, pp. 233-241, 1985.
Glowacki et al., "Fate of Mineralized and Demineralized Osseous Implants in Cranial Defects", Calcified Tissue Int. 33: 71-76, 1981.
Groeneveld et al., "Mineralized Processes in Demineralized Bone Matrix Grafts in Human Maxillary Sinus Floor Elevations", John Wiley & Sons, Inc. pp. 393-402 (1999).
Habal et al., "Autologous Corticocancellous Bone Paste for Long Bone Discontinuity Defects: An Experimental Approach", Annals of Plastic Surgery, Aug. 1985, vol. 15, No. 23, pp. 138-142.
Ito, Takayasu et al., "Sensitivity of Osteoinductive Activity of Demineralized and Defatted Rat Femur to Temperature and Furation of Heating", Clinical Orthopaedics and Related Research, No. 316, 1995, pp. 267-275.
Jurgensen, K., M.D. et al., "A New Biological Glue for Cartilage-Cartilage-Cartilage Interfaces: Tissue Transglutaminase", Journal of Bone and Joint Surgery, Inc., Feb. 1997, pp. 185-193.
Kaban et al., "treatment of Jaw Defects with Demineralized Bone Implants", Journal of Oral and Maxillofacial Surgery, pp. 623-626 (Jun. 6, 1998).

Kakiuchi et al., "Human Bone Matrix Gelatin as a Clinical Alloimplant", International Orthopaedics, 9, pp. 181-188 (1985).
Kiviranta et al., "The Rate fo Calcium Extraction During EDTA Decalcification from Thin Bone Slices as Assessed with Atomic Absorption Spectrophometry", Histochemistry 68, 1980, pp. 119-127.
Kubler, et al., "Allogenic bone and Cartilage Morphogenesis", J. Craniomaxillofac. Surg. 19(7): 238-288, 1991.
Lewandrowski et al., "Flexural Rigidity in Partially Demineralized Diaphysical Bone Grafts," *Clin. Ortho. Rel. Res.* 317: 254-262, 1995.
Lewandrowski et al., "Kinetics of Cortical Bone Demineralization: controlled demineralization—a new method for modifying cortical bone allografts," *J. Biomed. Mater. Res.* 31:365-372, 1996.
McLaughlin et al., "Enhancements of Bone Ingrowth by the Use of Bone Matrix as a Biologic Cement", Clinical Orthopaedics and Related Research, No. 183, pp. 255-261 (Mar. 1984).
Meijer et al., Radiographic Evaluation of Mandibular Augmentation with Prefabricated Hydroxylapatite/Fibrin Glue Imlants, Journal of Oral and Maxillofacial Surgery, 1997, pp. 138-145.
Mellonig, "Decalicified Freeze-Dried Bone Allograft as an Implant Material in Human Periodontal Defects", *The International Journal of Periodontics and Restorative Dentistry*, pp. 41-45, 1984.
Mellonig, James T. D.D.S., M.S., "Bone Allografts in Periodontal Therapy", Clinical Orthopaedics and Related Research, No. 324, Mar. 1996.
Mulliken, J.B. and Glowacki, "Induced Osteogenesis for Repair and Construction in the Craniofacial Region", J. Plastic and Reconstructive Surgery, May 1980, p. 553-559.
Neigal et al., "Use of Demineralized Bone Implants in Orbital and Craniofacial", Opthal. Plast. Reconstrs. Surg., 12: 108-120, 1996.
Paralkar, et al., PNAS, 100(11): 6736-6740, 2003.
Parma-Benfenati, S., et al., "Histologic Evaluation of New Attachment Utilizing a Titanium-Reinforced Barrier Membrane in a Nucogingival Recession Defect. A Case Report", J. Periodontology, Jul. 1998.
Perez, B.J. et al., "Mechanical properties of a discontinous random fiber composite for totally bioabsorbable fracture fixation devices", Paper presented in : Bioengineering Conference, 1995, Proceedings of the 1995 IEEE 21st Annual Northeast, May 22-23, 1995, pp. 55-56.
Product literature for Bio-Gide ©, Resorbable barrier membrane from OsteoHealth Co., Division of Luitpold Pharmaceutical, Inc. 1998.
Product literature for Gore Resolut XT, Bioabsorbable membrane from Gore Regenerative Technologies, Palm Beach Gardens, FL 1998.
Ray, Robert et al. "Bone Implants: Preliminary Report of an Experimental Study", Journal of Bone and Joint Surgery, vol. 29A (5), Oct. 1957.
Reddi et al., *Proc. Natl. Acad. Sci.* 69:1601-1605, 1972.
Russell et al., *Orthopaedics*, 22(5):524-53, May 1, 1999.
Stairs, Robert A. "Calculation of surface tension of salt solutions: effective polarizability of solvated ions." Can. J. Chem. 73: pp. 781-787 (1995).
Stevenson et al., "Factors Affecting Bone Graft Incorporation", Clinical Orthopaedics and Related Research, No. 323, 1996, pp. 66-74.
The Term "Substantially", Merriam-Webster Online Dictionary, at the web—http://www.m-w.com, p. 1.
Teparat, Thitiwan et al., "Clinical Comparison of Bioabsorbable Barriers With Non-Resorbable Barriers in Guided Tissue Regeneration in the Treatment of Human Intrabony Defects", J. Periodontology, Jun. 1998.
Todescan et al., "A Small Animal Model for Investigating Endosseous Dental lmpants:Effect of Graft Materials on Healing of Endoss, Porous-Surfaced Implants Placed in a Fresh Extraction Socket", *The Journal of Oral and Maxillofacial Implants*, vol. 2, No. 2, pp. 217-223, 1987.
Ueland et al., "Increased Cortical Bone Content of Insulin-Like Growth Factors in Acromegalic Patients", J. Clin. Endocrinol. Metab., 84(1): 123-127, 1999.
Urist, M.R. et al., "The Bone Induction Principle", *Clin. Orthop. Rel. Res.* 53:243-283, 1967.

Urist, M.R., "Bone Formation by Autoinduction", *Science*, 150(698):893-9, 1965.

Whiteman et al., *J. Hand. Surg.* 18B:487, 1993.

Whittaker et al., "Matrix Metalloproteinases and Their Inhibitors—Current Status and Future Challenges", Celltransmissions, 17(1): 3-14.

Xiaobo et al., *Orthop.*, No. 293, pp. 360-365, 1993.

Zhang, et al., "A Quantative Assessment of Osteoinductivity of Human Demineralized Bone Matrix", J. Periodontol. 68(11): 1076-1084, 1997.

Urist et al. "Bone Formation in Implants of Partially and Wholly Demineralized Bone Matrix," Clinical Orthopaedics and Related Research, vol. 71, pp. 271-278 (1970).

Grafton'™ Allogenic Bone Matrix (ABM), Advertising Brochure, Advanced Processing of Human AI log raft Bone, Osteotech, Inc., 1992.

Frenkel et al. "Use of Demineralized Bone Matrix Gel to Enhance Spine Fusion", 19th Annual Meeting of the Society for Biomaterials, Apr. 28-May 2, 1993, Birmingham, AL, p. 162.

Stevenson et al. "Long Bone Defect Healing Induced by a New Formulation of Rat Demineralized Bone Matrix Gel," 40th Annual Meeting, Orthopedic Research Society, Feb. 21-24, 1994, New Orleans, LA, p. 205-35.

Ruppert, Rainer et al. "Human bone morphogenetic protein 2 contains a heparin-binding site which modifies its biological activity," *Eur. J. Biochem*, 237(1): 295-302 (1996).

Kubler, N. R. et al. "EHBMP-2: The first BMP-variant with osteoinductive properties," *Mund Kiefer Gesichtschir*, 3(1): S134-S139 (1999).

Reddi, A. Hari. "Interplay between bone morphogenetic proteins and cognate binding proteins in bone and cartilage development: noggin, chordin and DAN," *Arthritis Research*, 3(1): 1-5(2001).

Gazzerro, Elisabetta et al. "Bone Morphogenetic Proteins Induce the Expression of Noggin, Which Limits Their Activity in Cultured Rat Osteoblasts," *Jour. ofClin. Invest*, 102(12): 2106-2114(1998).

Yamaguchi, Akira. "Recent advances in researches on bone formation—Role of BMP in bone formation," Nihon Rinsyo, 56(6): 1406-1411 (1998).

Dallas, Sarah L. et al. "Dual Role for the Latent Transforming Growth Factor-/? Binding Protein in Storage of Latent TGF-/7 in the Extracellular Matrix and as a Structural Matrix Protein," *Jour. ofCellBiol.*, 131(2): 539-549 (1995).

Pedrozo, Hugo A. et al. "Vitamin $D_3$ Metabolites Regulate LTBP1 and Latent TGF-/?1 Expression and Latent TGF-/71 Incorporation in the Extracellular Matrix of Chohdrocytes," *Jour, of Cell. Biochem.*, 72(1): 151-165 (1999).

Pedrozo, Hugo A. et al. "Growth Plate Chondrocytes Store Latent Transforming Growth Factor (TGF)- /?1 in Their Matrix Through Latent TGF-/?1 Binding Protein-1," *Jour, of Cellular Physiology*, 177(2): 343-354 (1997).

Bautista, Catalino M. et al. "Isolation of a novel insulin-like growth factor (IGF) binding protein from human bone: A potential candidate for fixing IGF-II in human bone," *Biochem. and Biophys. Research Communications*, 176(2): 756-763 (Apr. 30, 1991).

Mohan, S. "Insulin-Like Growth Factor Binding Proteins in Bone Cell Regulation," Growth Regulation, 3(1): 67-70 (1993).

Japanese Office Action dated Mar. 18, 2009, from related, co-pending application JP 2003-533987.

JADA, vol. 133, Dec. 2002. http://jada.ada.org/cgi/reprint/133/12/1610-a.

VOLUME MAINTAINING OSTEOINDUCTIVE/OSTEOCONDUCTIVE COMPOSITIONS

CROSS-REFERENCE TO RELATED APPLICATION

This application is a continuation application of U.S. application Ser. No.12/548,029, filed Aug. 26, 2009, now U.S. Pat. No. 800213 , which is a continuation of U.S. application Ser. No. 11/284,539, filed Nov. 22, 2005, which is a continuation of U.S. application Ser. No. 10/413,324, filed on Apr. 14, 2003, which is a continuation of International Application No. PCT/US2000/28462, filed on Oct. 13, 2000, which claims priority to U.S. Provisional Application No. 60/159, 774, filed on Oct. 15, 1999. The contents of all the above-identified applications are incorporated in their entirety by reference herein.

BACKGROUND OF THE INVENTION

This invention relates to an osteoinductive and osteoconductive composition containing demineralized fibrous bone elements in combination-with non-fibrous bone elements that are demineralized, partially demineralized or non-demineralized. More particularly, the invention relates to demineralized fibrous bone elements having a relatively high median length to median thickness ratio and relatively high surface area to volume ratio; demineralized, partially demineralized or non-demineralized non-fibrous bone elements that vary from "mostly irregular" to "mostly regular" in shape and not more than 10 mm in any measurable component of the shape to determine size, e.g., height, base, length, width, diameter or radius; and to a volume maintaining osteoinductive/osteoconductive composition containing such fibrous and non-fibrous elements within a biocompatible fluid carrier.

The use of pulverized exogenous bone growth material, e.g., derived from demineralized allogenic or xenogenic bone in the surgical repair or reconstruction of defective or diseased bone is known. See, in this regard, the disclosures of U.S. Pat. Nos. 4,394,370, 4,440,750, 4,472,840, 4,485,097, 4,678,470, and 4,743,259; Bolander et al., "The Use of Demineralized Bone Matrix in the Repair of Segmental Defects", The Journal of Bone and Joint Surgery, Vol. 68-A, No. 8, pp. 1264-1273; Glowackie et al, "Demineralized Bone Implants", Symposium on Horizons in Plastic Surgery, Vol. 12, No. 2; pp. 233-241(1985); Gepstein et al., "Bridging Large Defects in Bone by Demineralized Bone Matrix in the Form of a Powder", The Journal of Bone and Joint Surgery, Vol. 69-A, No. 7, pp. 984-991(1987); Mellonig, "Decalcified Freeze-Dried Bone Allograft as an Implant Material In Human Periodontal Defects", The International Journal of Periodontics and Restorative Dentistry, pp. 41-45 (June, 1984); Kaban et al., "Treatment of Jaw Defects with Demineralized Bone Implants", Journal of Oral and Maxillofacial Surgery, pp. 623-626 (Jun. 6, 1989); and, Todescan et al., "A Small Animal Model for Investigating Endosseous Dental Implants: Effect of Graft Materials on Healing of Endosseous, Porous-Surfaced Implants Placed in a Fresh Extraction Socket", The International Journal of Oral & Maxillofacial Implants Vol. 2, No. 4, pp. 217-223 (1987). According to Kakincki et al., "Human bone matrix gelatin as a clinical alloimplant", International Orthopaedics, 9, pp. 181-188 (1985), a water insoluble osteoinductivelosteoconductive substance referred to therein as "bone matrix gelatin" which was obtained by decalcifying (ire., demineralizing) bone was successfully employed as an alloimplant for the treatment of bone defects and other disorders. An apparently similar water insoluble osteoinductive/osteoconductive material, referred to as "decalcified bone matrix", is disclosed in McLaughlin et al., "Enhancement of Bone Ingrowth by the Use of Bone Matrix as a Biologic Cement", Clinical Orthopaedics and Related Research, No. 183, pp. 255-261 (March, 1984). However, the prior art demineralized bone products have proven to be unsatisfactory for applications requiring a bone product, which maintains the volume of bone defect sites and allows for firm packing. Thus, an osteoinductive/osteoconductive composition, which maintains its cohesiveness and volume and resists erosion, would be highly desirable.

BRIEF SUMMARY OF THE INVENTION

It is an object of the invention to provide a quantity of demineralized fibrous bone elements, a quantity of non-fibrous bone elements that are demineralized, partially demineralized or non-demineralized having a least dimension substantially larger than the thickness of the fibrous elements, and a cohesive osteoinductive/osteocon-ductive composition containing the fibrous and non-fibrous elements.

It is a further object of the invention to provide a cohesive osteoinductive/osteoconductive composition, which is capable of wicking up blood and body fluids from the implant site, mixtures of bone marrow aspirate, autograft, etc.

It is a further object of the invention to provide the cohesive osteoinductive/osteoconductive composition as an entangled mass with the non-fibrous elements maintained within the entangled fibrous elements of the composition.

It is a further object of the invention to provide a cohesive osteoinductive/osteoconductive composition with superior surgical handling properties, e.g., the ability to pick up globs of it with forceps in order to place it at a surgical site.

It is a further object of the invention to provide a volume maintaining osteoinductive/osteoconductive composition, which can be placed or injected into a hollow defect site.

It is a further object of the invention to provide an osteoinductive/osteoconductive composition having superior volume maintaining properties, e.g., the ability to be packed firmly into large defect sites.

It is a further object of the invention to provide an osteoinductive/osteoconductive composition that provides for rapid remodeling and incorporation of the non-fibrous elements into the host site, i.e., being turned into bone not only on the outside surfaces but also on the internal surfaces of the non-fibrous elements such that the composition remodels from inside out as well as outside in.

It is a further object of the invention to provide a method of treating trauma indications, e.g., tibia plateau fractures, such that when the tibia plateau is elevated back to its normal anatomical configuration, the crushed area of the metaphysis can be easily filled with the composition of this invention to establish a solid fill that contributes to the maintenance of this normal anatomical reconstruction.

It is a further object of the invention to provide an osteoinductive/osteoconductive composition in which the size and shape of the elements can be varied to suit the particular application.

It is a further object of the invention to provide an osteoinductive/osteoconductive composition in which the ratio of fibrous elements to non-fibrous elements to carrier can be varied to suit the particular application.

It is a further object of the invention to provide a composition that is capable of being viewed utilizing radiographic imaging techniques.

The stated objects of the invention are not intended to be limiting in any way. Of course further objects of the invention herein will be obvious to those skilled in the art in view of the above stated objects and the foregoing specification.

In keeping with these and related objects of the invention, there is provided an osteoinductive/osteoconductive composition comprising: (a) a quantity of fibrous bone elements possessing an average surface area to volume ratio of about 100:1 to about 20:1, (b) a quantity of non-fibrous bone elements possessing an average surface area to volume ratio of about 10:1 or less and (c) a quantity of biocompatible fluid carrier sufficient to provide the composition as a deformable mass. Application of the foregoing osteoinductive/osteoconductive composition to the site of a large bone defect, e.g., one resulting from injury, infection, disease, malignancy or developmental malformation, leads to rapid new bone ingrowth by one or more mechanisms such as osteogenesis, osteoinduction and/or osteoconduction.

The inclusion of fibrous bone elements (a) imparts a higher level of cohesiveness to the osteoinductive/osteoconductive composition of this invention compared with that of an osteoinductive/osteoconductive composition containing the same ratio of bone elements to carrier but in which the bone elements are all, or substantially all, of the non-fibrous variety, e.g., the compositions of U.S. Pat. No. 5,073,373. The inclusion of non-fibrous bone elements (b) provides an osteoinductive/osteoconducti-ve composition which requires a higher level of applied mechanical force to effect its deformation than that required to deform an osteoinductive/osteoconductive composition containing the same ratio of bone elements to carrier but in which all, or substantially all, of the bone elements possess a relatively high surface area to volume ratio, e.g., the osteoinductive/osteoconductive composition of aforesaid U.S. Pat. No. 5,314,476 in which all, or substantially all, of the bone elements are of the fibrous variety.

The expression "median length to median thickness ratio" as applied to the fibrous bone elements of the invention shall be understood to refer to the ratio of the longest median dimension of the fibrous bone element (its median length) to its shortest median dimension (its median thickness).

The term "cohesive" as applied to the osteoinductive/osteoconductiv-e composition of this invention shall be understood to refer to the ability of the composition to be shaped or packed into a coherent mass which retains its shape and volume and resists erosion from the implant site.

The term "fibrous" as applied to this invention refers to bone elements whose median length to median thickness ratio is at least about 10:1 and whose surface area to volume ratio is between about 100:1 and about 20:1. In overall appearance the fibrous bone elements can be described as fibers, threads, narrow strips, or thin sheets. Often, where thin sheets are produced, their edges tend to curl up toward each other. The fibrous bone elements can be substantially linear in appearance or they can be coiled to resemble springs. The fibrous bone elements are preferably demineralized however some of the original mineral content may be retained when desirable for a particular embodiment of the invention.

The expression "non-fibrous" as applied to the elements of this invention refers to elements that have a median width substantially larger than the median thickness of the fibrous bone element. Such non-fibrous bone elements will have a surface area to volume ratio significantly smaller than the fibrous bone elements, e.g., about 10:1 or less. Preferably the non-fibrous bone elements are shaped in a substantially regular manner or specific configuration, e.g. triangular prism, sphere, cube, cylinder and other regular shapes. By contrast, particles such as chips, shards, or powders possess irregular or random geometries. It should be understood that some variation in dimension will occur in the production of the elements of this invention and elements demonstrating such variability in dimension are within the scope of this invention and are intended to be understood herein as being within the boundaries established by the expressions "mostly irregular" and "mostly regular".

The expression "partially demineralized bone elements" as applied to this invention refers to bone elements that are demineralized to the extent that only a small amount of mineral remains in the core. That is the residual calcium is between about 50 to 100% by weight.

The expression "maintains its cohesiveness and volume and resists deformation" as applied to this invention refers to the ability of the composition to be packed into an appropriate size defect site and lock into place remaining as a coherent mass where it is placed. In addition, the invention resists substantial deformation when subjected to a force of up to about 10 N. This is in contrast to prior art compositions of paste-like or putty-like consistency as well as those of liquid or runny consistency.

BRIEF DESCRIPTION OF THE DRAWINGS

The following is a brief description of the drawings which are presented only for the purposes of further illustrating the invention and not for the purposes of limiting the same.

DETAILED DESCRIPTION OF THE INVENTION

Figure 1:
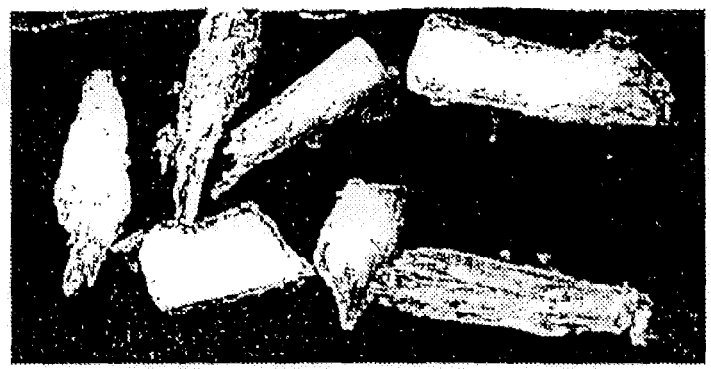
FIG. 1 are irregular non-fibrous bone elements, FIG. 1A are mostly regular non-fibrous bone elements prepared as in Example 1.
Figure 1A:
FIG. 1B represents a side-by-side comparison of the size and regular shape of the non-fibrous bone elements useful in the invention herein and the irregular non-fibrous elements of FIG. 1.
Figure 1B:
Figure 2:
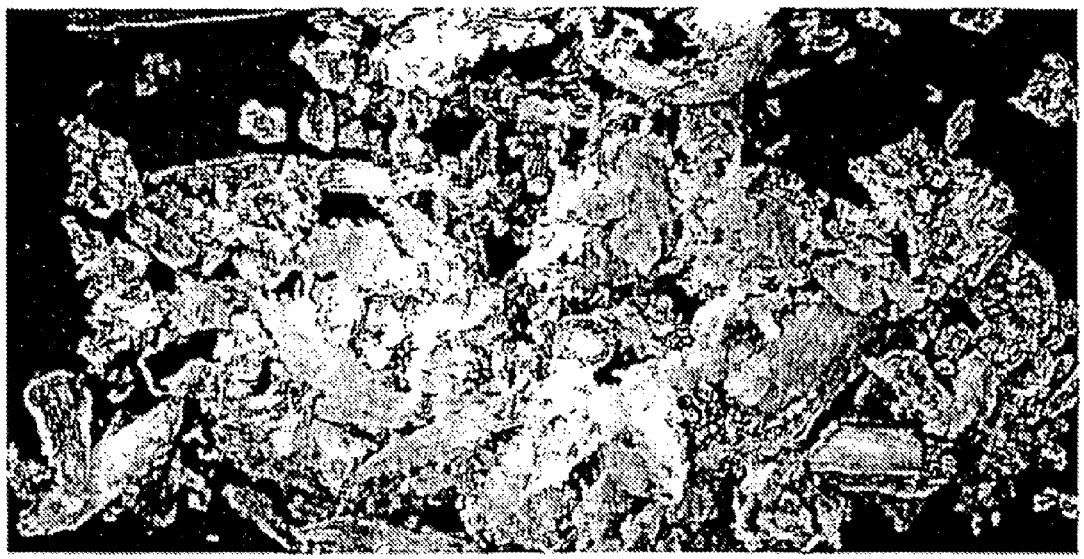
FIG. 2 represents the appearance of a prior art bone composition and FIG. 2A is a composition prepared as in Example 1.
Figure 2A:
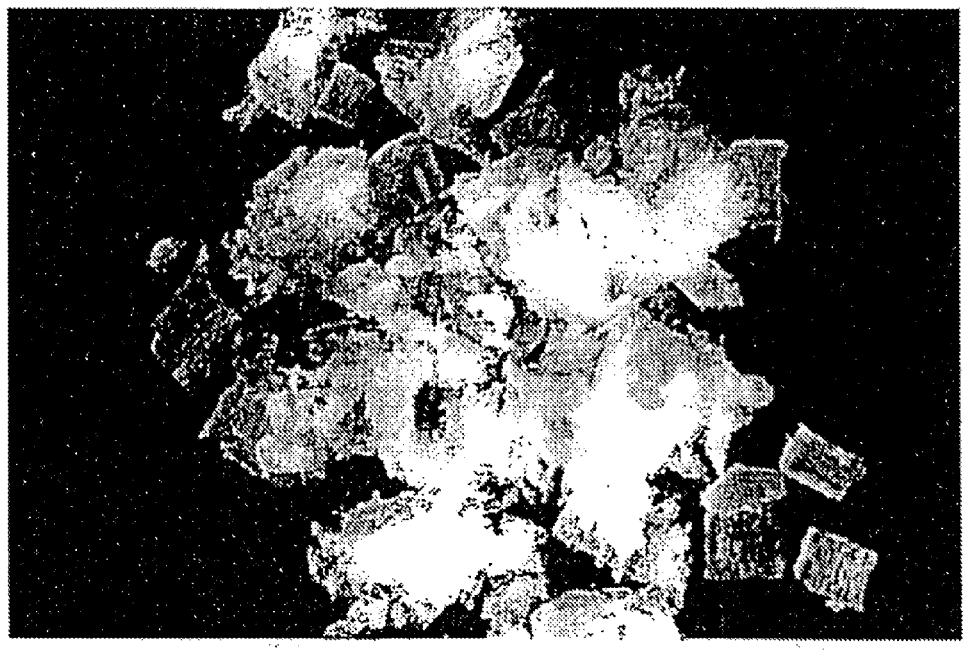
Figure 3:
FIG. 3 is a relatively large defect site and FIG. 3A demonstrates the ability of a composition prepared as in Example 1 to fill a relatively large defect site.
Figure 3A:
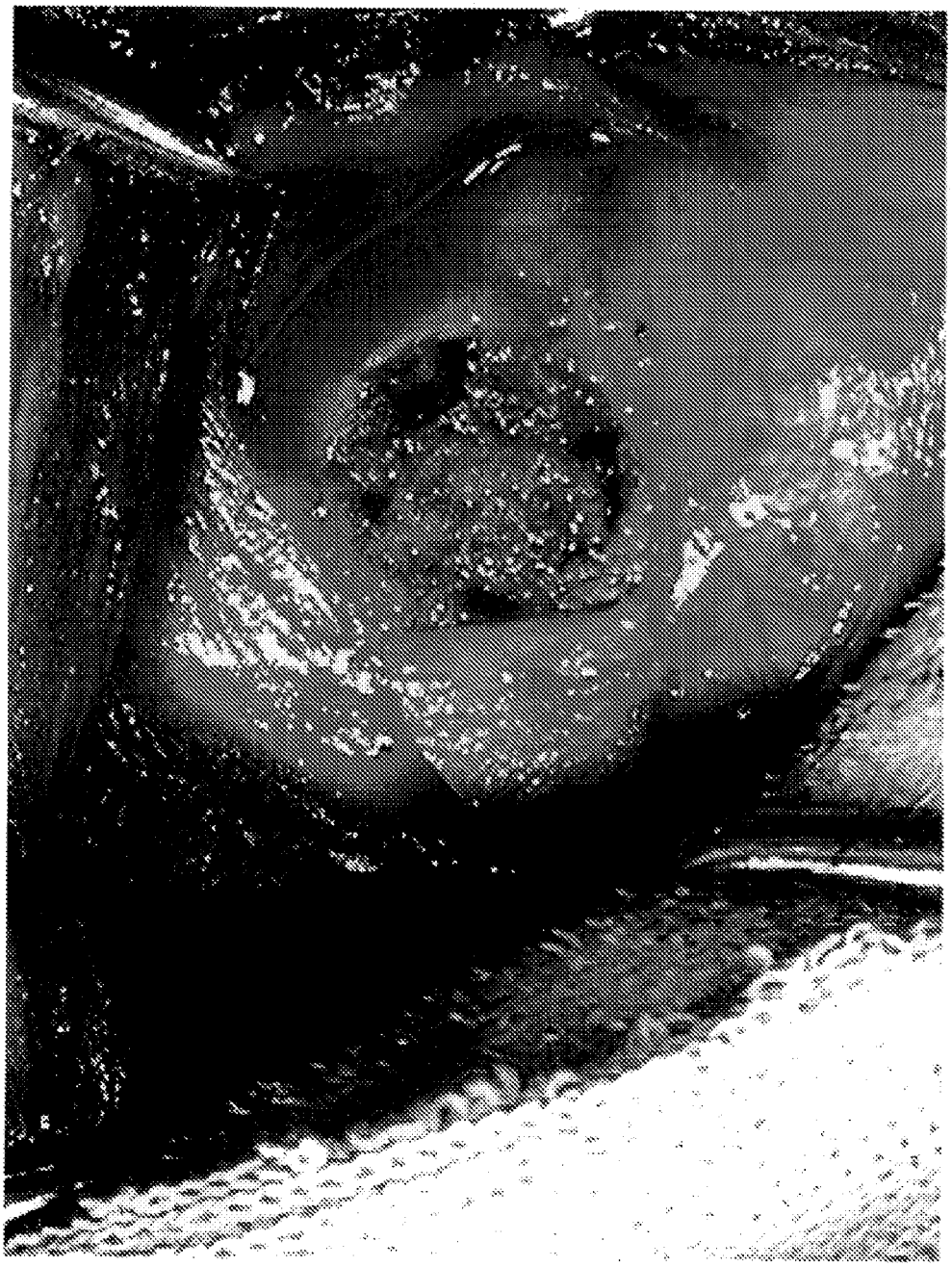
Figure 4:
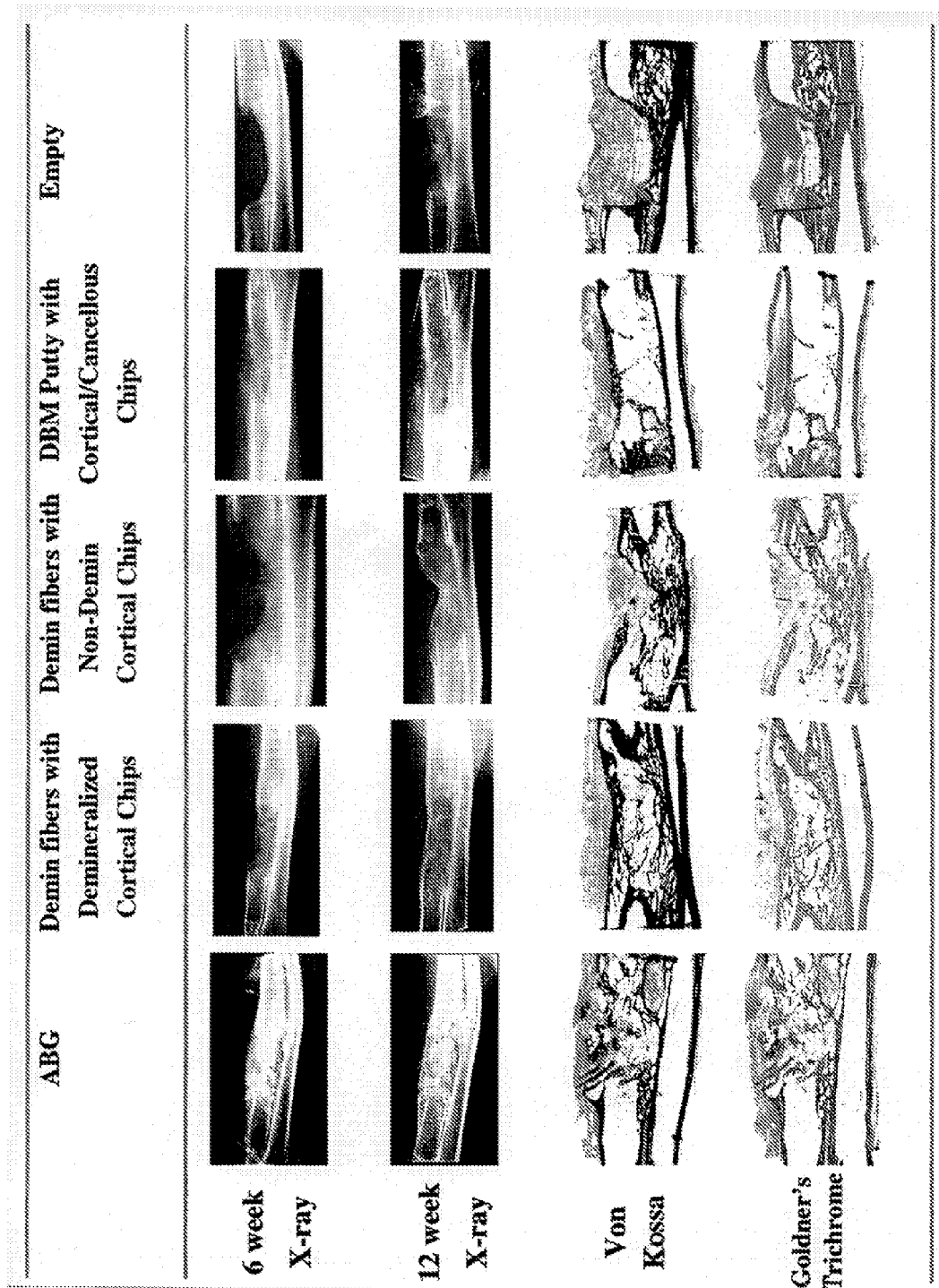
FIG. 4 represents the radiographic and biological results obtained in Example 4.

The bone utilized in this invention is obtained utilizing methods well known in the art, e.g., aseptically procured allogenic donor bone that has been cleaned and disinfected. Fibrous bone elements whose median length to median thickness ratio is at least about 10:1 can be readily obtained by any one of several methods, e.g., shaving the surface of an entire bone or relatively large section of bone. Employing a shaving technique, fibrous bone elements ranging in median length from about 2 mm up to 400 mm or more (as in the case of the long bones) and in median thickness from about 0.05 mm to about 2 mm can be obtained. An apparatus useful for obtaining the fibrous bone elements useful herein is described in U.S. Pat. No. 5,607,269 the contents of which are incorporated herein by reference.

Depending on the procedure employed for producing the fibrous bone elements, one can obtain a mass of fibrous bone elements containing at least about 50 weight percent, preferably at least about 70 weight percent and most preferably at least about 80 weight percent of the fibrous bone elements possessing a median length of from about 2 mm to about 400 mm or more and preferably from about 10 mm to about 100 mm, a median thickness of from about 0.05 mm to about 2 mm and preferably from about 0.08 mm to about 1.5 mm, and a median length to median thickness ratio of at least 10:1 up to about 500:1 or more and preferably from about 50:1 to about 100:1. The surface area to volume ratio of the fibrous bone elements will vary between about 100:1 and about 20:1, preferably between about 80:1 and about 40:1. If desired, the mass of fibrous bone elements bone can be graded into different sizes and/or any less desirable size(s) of fibrous bone elements which may be present can be reduced or eliminated. The fibrous bone elements can be obtained from cortical autogenic, cortical allogenic, cortical xenogenic, cortical transgenic, cancellous autogenic, cancellous allogenic, cancellous xenogenic, cancellous transgenic, corticocancellous autogenic, corticocancellous allogenic, corticocancellous xenogenic or corticocancellous transgenic bone. Porcine and bovine bone are a particularly advantageous type of xenogenic bone tissue which can be used as a source for the fibrous bone elements of this invention, although of course other sources of bone such as ovine, caprine and equine may also be suitable.

Following shaving, milling or other technique whereby they are optionally obtained, the fibrous bone elements are subjected to demineralization in order to reduce their inorganic content to a very low level, e.g., to not more than about 5% by weight of residual calcium and preferably to not more than about 1% by weight residual calcium. Demineralization of the fibrous bone elements ordinarily results in their contraction to some extent.

Demineralization of the fibrous bone elements can be conducted in accordance with known conventional procedures. For example, in a preferred demineralization procedure, the fibrous bone elements are subjected to an acid demineralization step that is followed by a defatting/disinfecting step. The bone is immersed in acid over time to effect its demineralization. Acids which can be employed in this step include inorganic acids such as hydrochloric acid and organic acids such as peracetic acid. After acid treatment, the bone is rinsed with sterile water for injection, buffered with a buffering agent to a final predetermined pH and then finally rinsed with water for injection to remove residual amounts of acid and buffering agent or washed with water to remove residual acid and thereby raise the pH. Following demineralization, the bone is immersed in solution to effect its defatting. A preferred defatting/disinfectant solution is an aqueous solution of ethanol, the ethanol being a good solvent for lipids and the water being a good hydrophilic carrier to enable the solution to penetrate more deeply into the bone. The aqueous ethanol solution also disinfects the bone by killing vegetative microorganisms and viruses. Ordinarily at least about 10 to 40 weight percent by weight of water (i.e., about 60 to 90 weight percent of defatting agent such as alcohol) should be present in the defatting/disinfecting solution to produce optimal lipid removal and disinfection within the shortest period of time. The preferred concentration range of the defatting solution is from about 60 to 85 weight percent alcohol and most preferably about 70 weight percent alcohol. Further in accordance with the invention, the demineralized fibrous bone elements can be used immediately for preparation of the osteoinductive/osteoconductive composition or they can be stored under aseptic conditions, advantageously in a lyophilized state prior to such preparation. In a preferred embodiment, the fibrous bone elements can retain some of their original mineral content such that the composition is rendered capable of being imaged utilizing radiographic techniques such as disclosed in U.S. Pat. No. 5,676,146 the contents of which are incorporated herein by reference.

The non-fibrous bone elements of this invention substantially display a relatively small surface area to volume ratio, e.g., less than about 10:1, preferably less than about 6:1, most preferably less than about 3:1. The median width of the non-fibrous bone elements is at least as large as the median thickness of the fibrous bone elements utilized in the composition of this invention but more preferably larger. In further accordance with some of the objects of this invention, the size and shape of the non-fibrous elements of the invention can be varied to tailor the composition to its intended application. In preferred embodiments, the composition will contain non-fibrous elements that exhibit a substantially larger least dimension than the least dimension of the fibrous bone elements. In a preferred embodiment, the non-fibrous bone elements will display a "mostly regular" geometry, i.e.; the shape of the non-fibrous bone elements is a triangular prism, sphere, cube, cylinder, other regular shape or a combination of these shapes. Such shapes displaying a substantially regular geometry are to be distinguished from chips, shards, and powders which may have a relatively small surface area to volume ratio but which due to their "mostly irregular" shape are unable to lock into place when used in a composition intended to repair an appropriate size defect site. When it is desirable to have an embodiment capable of being injected or placed through, for example, a cannula or other similar device into a defect site, the shape of the non-fibrous elements will be substantially spheroid. Such non-fibrous elements can be obtained from cortical autogenic, cortical allogenic, cortical xenogenic, cortical transgenic, cancellous autogenic, cancellous allogenic, cancellous xenogenic, cancellous transgenic, corticocancellous autogenic, corticocancellous allogenic, corticocancellous xenogenic or corticocancellous transgenic bone. Porcine and bovine bone are a particularly advantageous type of xenogenic bone tissue which can be used as a source for the non-fibrous bone elements of this invention, although of course, ovine, caprine and equine bone may be entirely suitable.

About 20 to about 80 weight percent of the non-fibrous bone elements of the invention are non-fibrous bone elements having a median length to median width to median height ratio of at least about 1:0.3:1 and up to about 1:1.5, a median length of from about 0.25 mm to about 10 mm, a median width of from about 0.25 mm to about 10 mm and a median height of from about 0.25 mm to about 10 mm, the median width being the smallest dimension of the non-fibrous element and the median height being the io largest dimension of the non-fibrous element. Such non-fibrous elements are prepared utilizing methods well known in the art, e.g., cutting, milling, stamping, grinding. The size and shape of the non-fibrous elements can vary depending on the specific application the composition is intended for, e.g., large trauma defects will require relatively large non-fibrous elements, whereas small dental defects, e.g., sinus lifts, three-wall defects, furcations, etc., will require relatively small non-fibrous elements. Such variation of size and shape of the non-fibrous bone elements to tailor the composition to the specific application is intended to be within the scope of this invention. The non-fibrous bone elements useful herein can be fully mineralized, partially demineralized, or fully demineralized (i.e., <5% calcium by weight). In a preferred embodiment of the invention, the composition contains from about 0 to about 50 percent by weight of the non-fibrous bone elements mineralized bone, from about 0 to about 80 percent by weight of the non-fibrous bone elements partially demineralized bone and from about 0 to about 100 percent by weight of the non-fibrous bone elements fully demineralized bone.

The bone utilized in making the non-fibrous elements of the invention can be fully mineralized, partially demineralized or fully demineralized prior to the preparation of the non-fibrous elements. In a preferred embodiment cortical bone is cut into slices, e.g., about 3 mm in width, and then demineralized to the extent that only a small amount of mineral remains in the core, i.e., less than 10% by weight residual calcium, preferably less than 5% by weight residual calcium. The bone is then cut with a stamping technique to yield substantially cuboid shapes about 3.times.3.times.3 mm in length, width and height. Optionally, mineralized bone is cut into substantially cuboid shapes with a band saw. The bone cubes are then demineralized using techniques well known in the art, e.g., such as those described above. After the non-fibrous elements are obtained they can be used immediately for preparation of the osteoinductive/osteoconductive composition or they can be stored under aseptic conditions, advantageously in a lyophilized or frozen state prior to such preparation.

To prepare an osteoinductive/osteoconductive composition utilizing the demineralized fibrous bone elements and non-fibrous bone elements of this invention, a quantity of the fibrous and non-fibrous elements are combined with an amount of biocompatible fluid carrier which will provide a coherent mass. The carrier can be any of a number of compounds and/or polymers, e.g., polymer sugars, proteins, long chain hydrophilic block copolymers, reverse phase block copolymers, hyaluronic acid, polyuronic acid, mucopolysaccharide, proteoglycan, polyoxyethylene, surfactants, e.g., the pluronics series of nonionic surfactants, and peptide thickener. Suggested classes of biocompatible fluid carrier would include polyhydroxy compound, polyhydroxy ester, fatty alcohol, fatty alcohol ester, fatty acid, fatty acid ester, liquid silicone, mixtures thereof, and the like.

Examples of suitable biocompatible fluid carrier include, but are not limited to:

(i) Polyhydroxy compound, for example, such classes of compounds as the acyclic polyhydric alcohols, non-reducing sugars, sugar alcohols, sugar acids, monosaccharides, disaccharides, water-soluble or water dispersible oligosaccharides, polysaccharides and known derivatives of the foregoing. Specific polyhydroxy compounds include, 1,2-propanediol, glycerol, 1,4,-butylene glycol trimethylolethane, trimethylolpropane, erythritol, pentaerythritol, ethylene glycols, diethylene glycol, triethylene glycol, tetraethylene glycol, propylene glycol, dipropylene glycol; polyoxyethylene-polyoxypropylene copolymer, e.g., of the type known and commercially available under the trade names Pluronic and Emkalyx; polyoxyethylene-polyoxypropylene block copolymer, e.g., of the type known and commercially available under the trade name Poloxamer; alkylphenolhydroxypolyoxyethylene, e.g., of the type known and commercially available under the trade name Triton, polyoxyalkylene glycols such as the polyethylene glycols, xylitol, sorbitol, mannitol, dulcitol, arabinose, xylose, ribose, adonitol, arabitol, inositol, fructose, galactose, glucose, mannose, sorbose, sucrose, maltose, lactose, maltitol, lactitol, stachyose, maltopentaose, cyclomaltohexaose, carrageenan, agar, dextran, alginic acid, guar gum, gum tragacanth, locust bean gum, gum arabic, xanthan gum, amylose, mixtures of any of the foregoing, and the like.

(ii) Polyhydroxy ester, for example, liquid and solid monoesters and diesters of glycerol can be used to good effect, the solid esters being dissolved up to the limit of their solubilities in a suitable vehicle, e.g., propylene glycol, glycerol, polyethylene glycol of 200-1000 molecular weight, etc. Liquid glycerol esters include monacetin and diacetin and solid glycerol esters include such fatty acid monoesters of glycerol as glycerol monolaurate, glyceryl monopalmitate, glyceryl monostearate, etc. An especially preferred carrier herein comprises glyceryl monolaurate dissolved in glycerol or a 4:1 to 1:4 weight mixture of glycerol and propylene glycol, poly (oxyalkylene) glycol ester, and the like.

(iii) Fatty alcohol, for example primary alcohols, usually straight chain having from 6 to 13 carbon atoms, including caproic alcohol, caprylic alcohol, undecyl alcohol, lauryl alcohol, and tridecanol.

(iv) Fatty alcohol ester, for example, ethyl hexyl palmitate, isodecyl neopentate, octadodecyl benzoate, diethyl hexyl maleate, and the like.

(v) Fatty acid having from 6 to 11 carbon atoms, for example, hexanoic acid, heptanoic acid, octanoic acid, decanoic acid and undecanoic acid.

(vi) Fatty acid ester, for example, polyoxyethylene-sorbitan-fatty acid esters; e.g., mono- and tri-lauryl, palmityl, stearyl, and oleyl esters; e.g., of the type available under the trade name Tween from Imperial Chemical Industries; polyoxyethylene fatty acid esters; e.g., polyoxyethylene stearic acid esters of the type known and commercially available under the trade name Myrj; propylene glycol mono- and di-fatty acid esters such as propylene glycol dicaprylate; propylene glycol dilaurate, propylene glycol hydroxy stearate, propylene glycol isostearate, propylene glycol laureate, propylene glycol ricinoleate, propylene glycol stearate, and propylene glycol caprylic-capric acid diester available under the trade name Miglyol; mono-, di-, and mono/di-glycerides, such as the esterification products of caprylic or caproic acid with glycerol; e.g., of the type known and commercially available under the trade name lmwitor; sorbitan fatty acid esters, e.g., of the type known and commercially available under the trade name Span, including sorbitan-monolauryl, -monopalmityl, -monostearyl, -tristearyl, -monooleyl and tri-olcylesters; monoglycerides, e.g., glycerol mono oleate, glycerol mono palmitate and glycerol monostearate, for example as known and commercially available under the trade names Myvatex, Myvaplex and Myverol, and acetylated, e.g., mono- and di-acetylated monoglycerides, for example, as known and commercially available under the trade name Myvacet; isobutyl tallowate, n-butylstearate, n-butyl oleate, and n-propyl oleate.

(vii) Liquid silicone, for example, polyalkyl siloxanes such as polymethyl siloxane and poly (dimethyl siloxane) and polyalkyl arylsiloxane.

In a preferred embodiment of the osteoinductive/osteoconductive composition, the liquid carrier is a liquid polyhydroxy compound, liquid polyhydroxy compound derivative, liquid solution of solid polyhydroxy compound, liquid solution of solid polyhydroxy compound derivative or mixtures thereof. If necessary or desirable, the liquid carrier can be dissolved or diluted with an appropriate solvent such that when combined with the fibrous and non-fibrous elements of the invention a composition capable of being shaped or packed into a coherent mass which retains its shape and volume over the relatively long term, e.g., until the bone formation and remodeling process is completed, is provided. Thus, the polyhydroxy compound or polyhydroxy derivatives can be a liquid in the pure or highly concentrated state at ambient temperature, e.g., 1.5-50.degree. C., or it can be a solid or semi-solid at this temperature in which case it becomes necessary to dissolve the material in a solvent such as water, physiological saline, ethanol, glycerol, glucose, propylene glycol, polyethylene glycol of from 200-1000 molecular weight, polyvinyl alcohol, etc. Of course, the liquid carrier can be made up of one or more liquid polyhydroxy compounds or derivatives in solution with one or more solid polyhdroxy compounds or derivatives.

Of the foregoing polyhydroxy compounds, glycerol and its liquid monesters and diesters, e.g. monacetin and diacetin, fructose, glucose and sucrose, and mixtures thereof are preferred. Where the polyhydroxy compound is a solid, e.g., sucrose, a solvent such as water, glycerol, polyethylene glycol of from 200-1000 average molecular weight, or mixture thereof is used to provide a cohesive solution or paste of the compound.

Where, in a particular osteoinductive/osteoconductive composition, the fibrous and/or non-fibrous elements exhibit a tendency to quickly or prematurely separate from the carrier component or to otherwise settle out from the composition such that application of a fairly homogeneous composition is rendered difficult or inconvenient, it can be advantageous to include within the composition an optional substance whose thixotropic characteristics prevent or reduce this tendency. Thus, e.g., where the carrier component is glycerol and separation of fibrous and/or non-fibrous bone elements occurs to an excessive extent where a particular application is concerned, a thixotropic agent such as a solution of polyvinyl alcohol, polyvinylpyrrolidone, cellulosic ester such as hydroxypropyl methylcellulose, carboxyl methylcellulose, pectin, food-grade texturizing agent, gelatin, dextran, collagen, starch, hydrolyzed polyacrylonitrile, hydrolyzed polyacrylamide, polyelectrolyte such as polyacrylic acid salt, hydrogels, chitosan, other materials that can suspend particles, etc., can be combined with the carrier in an amount sufficient to significantly improve the suspension-keeping characteristics of the composition.

If desired, the fibrous and/or non-fibrous bone elements of this invention can be modified in one or more ways, e.g., their protein content can be augmented or modified as described in U.S. Pat. Nos. 4,743,259 and 4,902,296 the contents of which are incorporated herein by reference. Any of a variety of medically and/or surgically useful optional substances can be incorporated in, or associated with, the bone elements before, during, or after preparation of the osteoinductive/osteoconductive composition. Thus, e.g., one or more of such substances can be introduced into the bone elements, e.g., by soaking or immersing the bone elements in a solution or dispersion of the desired substance(s), by adding the substance(s) to the carrier component of the osteoinductive/osteoconductive composition or by adding the substance(s) directly to the osteoinductive/osteoconductive composition.

Medically/surgically useful substances which can be readily combined with the bone elements, fluid carrier and/or osteoinductive/osteoconductive composition of this invention include, e.g., demineralized bone powder as described in U.S. Pat. No. 5,073,373 the contents of which are incorporated herein by reference, collagen, insoluble collagen derivatives, hydroxyapatite, etc., and soluble solids and/or liquids dissolved therein, e.g., antiviricides, particularly those effective against HIV and hepatitis; antimicrobials and/or antibiotics such as erythromycin, bacitracin, neomycin, penicillin, polymyxin B, tetracyclines, viomycin, chloromycetin and streptomycins, cefazolin, ampicillin, azactam, tobramycin, clindamycin and gentainycin; etc.; amino acids, peptides, vitamins, inorganic elements, inorganic compounds, cofactors for protein synthesis, hormones; endocrine tissue or tissue fragments; synthesizers; enzymes such as collagenase, peptidases, oxidases, etc.; polymer cell scaffolds with paraenchymal cells; angiogenic drugs and polymeric carriers containing such drugs; collagen lattices; biocompatible surface active agents; antigenic agents; cytoskeletal agents; cartilage fragments, living cells such as chondrocytes, bone marrow cells, mesenchymal stem cells, natural extracts, tissue transplants, bioadhesives, bone morphogenic proteins (BMPs), transforming growth factor (TGF-beta), insulin-like growth factor (IGF-1) (IGF-2), platelet derived growth factor (PDGF), fibroblast growth factors (FGF), vascular endothelial growth factor (VEGF), angiogenic agents, bone promoters, cytokines, interleukins, genetic material, genes encoding bone promoting action, cells containing genes encoding bone promoting action; growth hornones such as somatotropin; bone digestors; antitumor agents; fibronectin; cellular attractants and attachment agents; immuno-suppressants; permeation enhancers, e.g., fatty acid esters such as laureate, myristate and stearate monesters of polyethylene glycol, surface active agents, enamine derivatives, .alpha.-keto aldehydes, etc.; nucleic acids; epidermal growth factor (EGF); all collagen types (not just type 1); non-collagenous proteins such as osteopontin, osteonectine, bone sialo proteins, vitronectin, thrombospondin, proteoglycans, decorin, biglycan, aggrecan, versican, tenascin, matrix gla protein hyaluronan; soluble and insoluble components of the immune system, soluble and insoluble receptors including truncated forms, soluble, insoluble and cell surface bound ligands including truncated forms; chemokines, bioactive compounds that are endocytosed; compounds capable of altering the membrane potential of cells, compounds capable of altering the monovalent and divalent cation/anion channels of cells; bone resportion inhibitors and stimulators; angiogenic and mitogenic factors; bioactive factors that inhibit and stimulate second messenger molecules; integrin adhesion molecules; clotting factors; externally expanded autograft or xenograft cells and any combinations thereof. The amounts of such optionally added substances can vary widely with optimum levels being readily determined in a specific case by routine experimentation.

As previously indicated, the osteoinductive/osteoconductive composition of this invention can be freshly prepared just by mixing desired quantities of the demineralized fibrous bone elements, non-fibrous bone elements, fluid carrier and optional component(s), if any, in any suitable sequence of separate mixing, adsorption, rehydration or drying operations or all at once. Thus, the demineralized fibrous bone elements and/or non-fibrous bone elements can be mixed with the optional ingredients(s) and thereafter combined with the fluid carrier component, the demineralized fibrous bone elements and/or non-fibrous bone elements can be mixed with the fluid carrier followed by addition of the optional ingredient(s) or the optional ingredients can be added to the fluid carrier followed by addition of the demineralized fibrous bone elements and/or non-fibrous bone elements. Variations of these and other sequences of mixing are, of course, possible. Advantageously, the fibrous and non-fibrous elements and fluid carrier are mixed substantially simultaneously such that the fibrous elements of the osteoinductive/osteoconductive composition are entangled and the non-fibrous bone elements are thoroughly mixed in the entangled fibrous bone elements.

The amount of demineralized fibrous bone elements which can be incorporated into the osteoinductive/osteoconductive composition can vary widely with amounts of from about 5 to about 90 weight percent, and preferably from about 20 to about 70 weight percent, being entirely suitable in most cases. Likewise, the amount of the non-fibrous bone elements which can be incorporated into the osteoinductive/osteoconductiv-e composition can very widely with amounts of from about 10 to about 90 weight percent, and preferably from about 20 to about 70 weight percent, being entirely suitable in most cases. The ratio of fibrous to non-fibrous bone elements can vary between about 0.2:1 to about 1:0.2. The balance of the composition being made up of fluid carrier and optional ingredient(s), if any.

In embodiments where it is desirable to improve the ability of the osteoinductive/osteoconductive composition to be imaged, e.g., by x-ray, radiopaque material(s) may be incorporated into the composition. Such materials would include, e.g., barium sulfate, iodine-containing compounds, titanium and mineralized bone.

To facilitate on-site preparation and/or usage of the composition herein, the demineralized fibrous bone elements and non-fibrous bone elements, preferably in lyophilized or frozen form, and fluid carrier (the latter containing one or more optional ingredients such as those identified above) can be stored in separate packages or containers under sterile conditions and brought together in intimate admixture at the moment of use for immediate application to an osseous defect site employing any suitable means such as spatula, forceps, syringe, tamping device, etc. Alternatively, the osteoinductive/osteoconductive composition can be prepared well in advance and stored under sterile conditions until required for use. When the osteoinductive/osteoconductiv-e composition is prepared well in advance it is preferably lyophilized prior to packaging for storage. At the time just prior to placing the osteoinductive/osteoconductive composition of the invention is to be placed in a defect site optional materials, e.g., autograft bone marrow aspirate, autograft bone, preparations of selected autograft cells, autograft cells containing genes encoding bone promoting action, etc., can be combined with the composition of this invention. Preferably, the osteoinductivelosteoconductive composition is packaged already mixed and ready for use in a suitable container, e.g., syringe, resealable non-toxic bottle, etc., or is provided as a kit which can be prepared at a surgeon's direction when needed.

The osteoinductive/osteoconductive composition of this invention can be firmly placed into an appropriate size defect site to maintain volume and provide support for adjacent tissues. Such placement can be accomplished through the use of a variety of devices such as, e.g., spatula, forceps, syringe, tamping device, etc.

The osteoinductive/osteoconductive composition of this invention can be tailored to be utilized for a variety of orthopaedic, neurosurgical, and oral and maxillofacial surgical indications in which it would be advantageous to be able to firmly place the composition into a bone defect site such as the repair of simple and compound fractures and nonunions, external fixations, joint reconstructions such as arthrodesis, general arthroplasty, acetabular repair, cup arthroplasty of the hip, femoral and humeral head replacement, femoral head surface replacement and total joint replacements, repairs of the vertebral column including spinal fusion and internal fixation, tumor surgery, e.g., deficit filling, discectomy, lain inectomy, excision of spinal cord tumors, anterior cervical and thoracic operations, repair of spinal injuries, scoliosis, lordosis and kyphosis treatments, intermaxillary fixation of fractures, mentoplasty, temporomandibular joint replacement, alveolar ridge augmentation and reconstruction, inlay bone grafts, implant placement and revision, sinus lifts, furcation defects, periodontal defects, dental defects, ulna defects, metaphyseal defects, tibia plateau defects, wrist defects, ankle defects, etc.

The invention will be more fully understood by way of the following examples which are intended to illustrate but not limit methods of preparation of the demineralized fibrous bone elements and non-fibrous bone elements of the invention and the preparation of an osteoinductive/osteoconductive composition containing the fibrous and non-fibrous elements in accordance with the present invention. A comparison of the compressive force of prior art compositions and the composition of the invention is also provided, however, this comparison is intended to illustrate but not limit the differences between this invention and the prior art.

EXAMPLE 1

Sections of defatted, disinfected allogenic cortical bone approximately 210-250 mm in length were cut on a band saw to yield 145.65 g of cuboid non-fibrous bone elements about 3 mm in size. The remaining allogenic cortical bone was processed in the bone milling apparatus described in U.S. Pat. No. 5,607,269 to yield 145.8 grams of fibrous bone elements. The non-fibrous bone elements were then placed in a reactor. A 0.6 N solution of HCl at 15 ml per gram of non-fibrous bone elements was introduced into the reactor, the reaction proceeded for 1 to 2 hours. Following drainage of the HCl, the non-fibrous bone elements were covered with 0.6 N HCl/20 ppm-2000 ppm nonionic surfactant solution for 24 to 48 hours. The fibrous bone elements were then added to the reactor and allowed to soak for 5 to 10 minutes. Following drainage of the HCl/surfactant solution, 0.6 N HCl at 15 ml per gram of total bone was introduced into the reactor, the reaction proceeded for 40 to 50 minutes. Following drainage through a sieve the bone was rinsed three times with water for injection at 15 ml per gram non-fibrous element weight with the water for injection being replaced at 15-minute intervals. Following drainage of the water for injection, the bone was covered with alcohol and allowed to soak for at least 30 minutes. The alcohol was then drained and the bone was rinsed with water for injection. The bone was then contacted with a mixture of 3.5 ml of glycerol per gram of dry bone and 5 ml of water for injection per gram of dry bone for at least 2 hours. After draining, the composition was transferred to a lyophilization tray and frozen at −70.degree. C. for at least 6 hours. The composition was then lyophilized following standard procedures for 24 to 48 hours.

EXAMPLE 2

The compressive force of the composition prepared as in Example 1 was compared with that of a like quantity of an osteoinductive/osteocondu-ctive composition prepared in accordance with U.S. Pat. No. 5,073,373 and an osteoinductive/osteoconductive composition prepared in accordance with U.S. Pat. No. 5,314,476. In this example, 5 cc of each material was placed into separate 10 cc syringe barrels. The compressive force (i.e., the sustained force capable of deflecting a meter probe) was then measured using the meter, to determine deflective force. The results are contained in the following table.

| Material | Compressive Force (N) |
| --- | --- |
| U.S. Pat. No. 5,073,373 | 4.8 |
| U.S. Pat. No. 5,314,476 | 7.9 |
| Example 1 | 10.3 |

EXAMPLE 3

Material prepared as in Example 1 was evaluated to determine its osteoinductive potential. The material was implanted in female athymic homozygous rnu/rnu rats according to the procedure described in Edwards et al., Osteoinduction of Human Demineralized Bone: Characterization in a Rat Model, Clinical Orthopedics and Related Research (No. 357, pp. 219-228) 1998, the contents of which are incorporated hereby by reference. The material was studied to analyze its bone formation response. After 28 days in the rat model it was determined that cells had accumulated in the porous region inside of the chips, differentiated into bone forming cells, and were in the process of laying down bone in remodeling the matrix from the inside out.

EXAMPLE 4

Twenty-four 6 month-old (3.5-4.0 kg) male New Zealand white rabbits (Covance: Denver, Pa.) were used. The animals received a standard rabbit diet (Purina, Ind.) and received standard tap water ad libitum. The animals were kept on a 12 h light/dark cycle.

The animals underwent surgery to create bilaterial 1.5 cm ulnar defects by the method described by Bostrom et al., Use of Bone morphogenic Protein-2 in the Rabbit Ulnar Nonunion Modelz, Clinical Orthopedics and Related Research (No. 327, pp. 272-282) 1996, the contents of which are incorporated herein by reference. The 48 defects were randomly assigned and implanted with one of the four grafting materials (Table 1). The final volume of each implant was 1 cc. The animals were not restricted from full weight bearing after surgery.

TABLE 1

| TREATMENT GROUP | EVALUATION PERIODS | SAMPLE SIZE |
| --- | --- | --- |
| 1 cc of autogenous bone graft from the iliac crest | 6 and 12 weeks | N = 1 at 6 weeks |
| Demineralized fibers with demineralized cortical chips | 6 and 12 weeks | N = 9 at 12 weeks |
| Demineralized fibers with non-demineralized cortical chips | 6 and 12 weeks | N = 3 at 6 weeks<br>N = 8 at 12 weeks |
| DBM Putty with non-demineralized cancellous chips | 6 and 12 weeks | N = 3 at 6 weeks<br>N = 9 at 12 weeks |
| Empty | 12 weeks | N = 2 at 12 weeks |

The animals were sedated and serial radiographs of the forelimbs were taken every three weeks until 12 weeks postoperatively when the animals were sacrificed. At the time of sacrifice, the ulnas were removed, cleaned of soft tissue, and radiographed using a high resolution Faxitron. Bony union (Table 2) and quantitative bone formation (Table 3) was evaluated at each time point by 3 independent, blinded observers. Bony union was defined as bridging of the defect in excess of 25% of the diaphyseal diameter. The radiographs were digitized to normalize the bone area and intensity so that bone formation could be quantified using image analysis software. Bone formation was evaluated on a standardized 5-point scale measuring percent of new bone seen in defect: 0=no new bone evident in defect, 1=1-25%, 2=26-50%, 3=51-75%, 4=76-99%, 5=100%.

TABLE 2

RADIOGRAPHIC UNIONS BY TIME POINT

| | 9 Weeks | | 12 Weeks | |
| --- | --- | --- | --- | --- |
| TREATMENT GROUP | Union | Nonunion | Union | Nonunion |
| Autograft | 5 | 4 | 8 | 1 |
| Demin Fibers/Demin Cortical Chips | 1 | 7 | 7 | 1 |
| DBM Putty/Non-Demin C/C Chips | 2 | 6 | 7 | 1 |
| Demin Fibers/Non-Demin Cortical Chips | 0 | 9 | 6 | 3 |

TABLE 3

BONE FORMATION EVALUATED RADIOGRAPHICALLY AREA OF DEFECT OCCUPIED BY BONE (MEDIAN SCORE)

| TREATMENT GROUP | Week 3 | Week 6 | Week 9 | Week 12 |
| --- | --- | --- | --- | --- |
| Autograft | 0 | 4 | 4 | 5 |
| Demin Fibers/Demin Cortical Chips | 0 | 3 | 3.5 | 4 |
| DBM Putty/Non-Demin C/C Chips | 1 | 3 | 4 | 4 |
| Demin Fibers/Non-Demin Cortical Chips | 1 | 3 | 3 | 4 |

All limbs from each group were prepared for histological analysis. Tissue samples were dehydrated over a course of several weeks with daily changes of the alcohol solutions. After dehydration was complete, tissue samples were embedded in methylmethacrylate. The blocks were cut in the longitudinal direction of the bone in 5.mu.m sections using a microtome. Serial sections were stained with one of the following stains: Hematoxylin and eosin, Goldner-Masson trichrome, or Von Kossa. The sections were examined for cellular characteristics indicative of new bone formation and callus formation. Groups using the Fisher's exact test compared radiographic union data. Bone formation was verified with a nonparametric analysis of variance (ANOVA), the Kruskal-Wallis H-test.

Experimental protocols were followed without incidence. There was one postoperative death resulting in the loss of 2 experimental defects. One defect was lost from demineralized fibers and demineralized cortical chips. Radiographic evaluation showed no statistically significant differences between the four groups. Some bone formation was evident in all groups by six weeks. At 12 weeks, all groups displayed similar quantities of new bone formation as assessed by radiodensity scale. (Table 3).

Union of the defect sites occurred in a similar fashion in all groups (Table 2). The autogenous bone graft ("ABG") group did show higher union rates at earlier point times, but at 12 weeks there is no statistically significant difference between the three groups. Strong bony bridges were seen in all four groups at 12 weeks. The only exceptions were in the demineralized fibers with non-demineralized chip. In this group, though 6 out of 9 were united, the defects tended not to have maintained their three-dimensional space and showed sagging in the middle.

It shall be understood, however, that the scope of the present invention is not to be limited to the specific embodiments described above. The invention may be practiced other than as particularly described and still be within the scope of the accompanying claims.

The invention claimed is:

1. A method of repairing a bone defect site comprising administering, at that site of the bone defect, an osteoinductive and osteoconductive composition comprising a cohesive entangled mass comprising (a) a quantity of demineralized fibrous bone elements possessing an average surface area to volume ratio of about 100:1 to about 20:1 and (b) a quantity of non-fibrous bone elements possessing an average surface area to volume ratio of about 10:1 or less, wherein a least dimension of the non-fibrous bone elements is larger than a least dimension of the fibrous bone elements and wherein the composition withstands a compressive force greater than 7.9 M without substantial deformation.

2. The method of claim 1, wherein the bone defect requires maxillofacial surgical treatment.)

3. The method of claim 1, wherein the bone defect requires neurosurgical treatment.

4. The method of claim 1, wherein the bone defect requires orthopedic treatment.

5. The method of claim 1, wherein the composition has a ratio of fibrous to non-fibrous elements of from about 0.2:1 to about 1:0.2.

6. The method of claim 1 wherein the composition is packed into the defect site utilizing at least one means selected from the group consisting of spatula, forceps, syringe and dental equipment.

7. The method of claim 1 wherein the defect site is selected from the group consisting of ulna defects, metaphyseal defects, tibia plateau defects, acetabular defects, sinus defects, long bone cortical defects, cranial defects, ilium defects, wrist/hand defects, ankle/foot defects and oral/maxillofacial defects.

8. The method of claim 1 wherein the composition further comprises at least one additive selected from the group consisting of autograft bone marrow aspirate, autograft bone, autograft cell preparations, autograft cells containing genes encoded for bone stimulating activity and autograft cells expanded outside the body and returned.

\* \* \* \* \*